US005741951A

United States Patent [19]
Preston

[11] Patent Number: 5,741,951
[45] Date of Patent: Apr. 21, 1998

[54] CONJOINT MANUFACTURE OF MTBE AND DIISOBUTYLENE

[75] Inventor: Kyle Lee Preston, Port Arthur, Tex.

[73] Assignee: Huntsman Specialty Chemicals Corporation, Austin, Tex.

[21] Appl. No.: 778,204

[22] Filed: Dec. 30, 1996

Related U.S. Application Data

[63] Continuation-in-part of Ser. No. 512,615, Aug. 8, 1995, abandoned.

[51] Int. Cl.$^6$ .................... C07C 41/09; C07C 41/05
[52] U.S. Cl. .................. 568/698; 568/697; 568/699
[58] Field of Search .................... 568/697, 698, 568/699

[56] References Cited

U.S. PATENT DOCUMENTS

| | | | |
|---|---|---|---|
| 4,144,138 | 3/1979 | Rao et al. | 203/46 |
| 5,243,091 | 9/1993 | Kruse et al. | 568/697 |
| 5,292,964 | 3/1994 | Gupta | 568/697 |
| 5,354,912 | 10/1994 | Hwan et al. | 568/697 |
| 5,386,065 | 1/1995 | Kruse et al. | 568/698 |
| 5,387,721 | 2/1995 | Kruse et al. | 568/697 |
| 5,395,982 | 3/1995 | Cassata et al. | 568/699 |

*Primary Examiner*—Marianne M. Cintins
*Assistant Examiner*—Dwayne C. Jones
*Attorney, Agent, or Firm*—Russell R. Stolle; Ron D. Brown; Carl G. Ries

[57] ABSTRACT

Methyl tertiary butyl ether and diisobutylene are prepared by reacting methanol with tertiary butyl alcohol to provide an etherification reaction product containing methyl tertiary butyl ether, tertiary butyl alcohol, methanol, isobutylene, and water. A methyl tertiary butyl ether product fraction and an isobutylene fraction are recovered from the etherification reaction product; the isobutylene fraction is charged to an isobutylene conversion reaction zone to form a diisobutylene conversion product, and the diisobutylene conversion product is charged to a diisobutylene distillation zone and separated therein into a lower boiling distillation fraction comprising isobutylene, and diisobutylene and a higher boiling distillation fraction consisting essentially of diisobutylene.

7 Claims, 1 Drawing Sheet

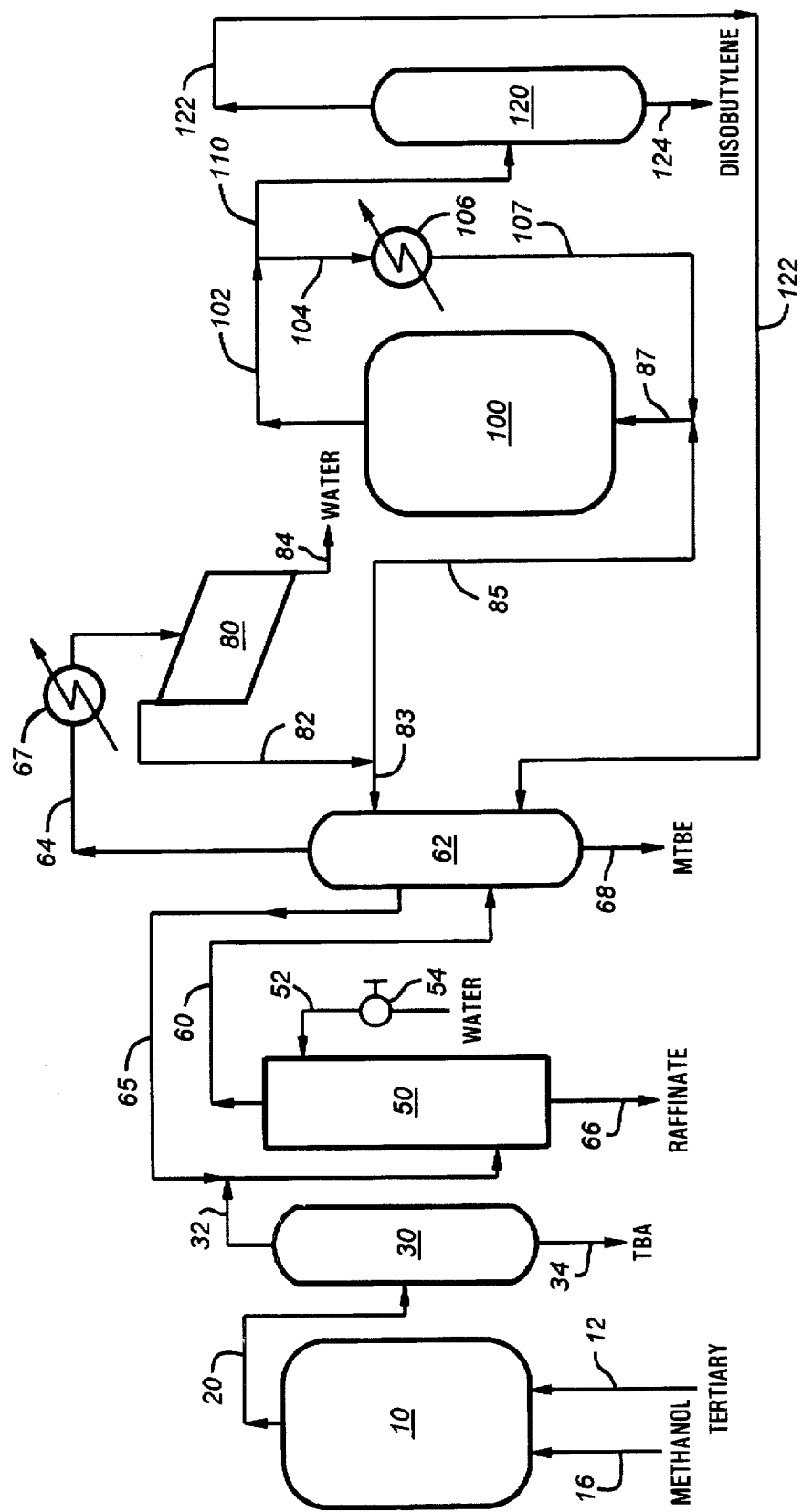

५,७४१,९५१

CONJOINT MANUFACTURE OF MTBE AND DIISOBUTYLENE

This application is a continuation-in-part of Preston U.S. Pat. application Ser. No. 08/512,615 filed Aug. 8, 1995, now abandoned and entitled "MANUFACTURE OF MTBE AND ISOBUTYLENE."

BACKGROUND OF THE INVENTION

Technical Field of the Invention

This invention relates to a method for the manufacture of methyl tertiary butyl ether (MTBE) and diisobutylene from tertiary butyl alcohol and methanol. More particularly, this invention relates to a method for the manufacture of methyl tertiary butyl ether and diisobutylene by the sequential reaction of methanol with tertiary butyl alcohol to produce MTBE and isobutylene, to the recovery and dimerization of the isobutylene to provide diisobutylene and to the purification of the methyl tertiary butyl ether and diisobutylene formed by the reactions.

Background Information

Methyl tert-butyl ether is finding increasing use as a blending component in high octane gasoline as the current gasoline additives based on lead and manganese are phased out. Diisobutylene is a valuable raw material for use in chemical reactions.

Prior Art

It is known to react tertiary butyl alcohol with methanol to provide a reaction product comprising MTBE, methanol and isobutylene as shown, for example, by Kruse U.S. Pat. No. 5,243,091, by Cassata et al. U.S. Pat. No. 5,395,982, by Hwan et al. U.S. Pat. No. 5,354,912, etc., by Kruse et al. U.S. Pat. No. 5,386,065, by Kruse et al. U.S. Pat. No. 5,387,721, etc. In the processes disclosed by these patentees methanol is reacted with tertiary butyl alcohol to form a reaction product that is distilled to provide a distillate fraction containing MTBE, methanol and isobutylene. The isobutylene contained in the distillate fraction is reacted with methanol to form additional MTBE in a second finishing reactor and the finishing reactor product is washed with water in a water washing tower to separate unreacted methanol from the MTBE, unreacted isobutylene and water. The unreacted isobutylene is recovered for recycle to the water washing tower and to the finishing reactor.

Gupta U.S. Pat. No. 5,292,964 also discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lower boiling (lighter) fraction comprising substantially anhydrous methanol and methyl tertiary butyl ether and a higher boiling (heavier) fraction comprising tertiary butyl alcohol, methanol and water, and wherein the lower boiling (lighter) fraction is charged to a finishing reactor wherein the methanol is reacted with isobutylene to form additional methyl tertiary butyl ether.

In U.S. Pat. No. 4,144,138 (1979) to Rao et al., there is disclosed a method for recovering methyl tertiary butyl ether from etherification reaction effluent by azeotropic distillation to recover a methanol-ether azeotrope overhead which is water-washed to give pure ether raffinate, the latter being azeotropically distilled to yield an ether-methanol overhead which is recycled to water washing.

It is known to react methanol with tertiary butyl alcohol in the presence of a catalyst in order to produce methyl tertiary butyl ether. A wide variety of catalysts have been suggested for this purpose.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

$$M_{2/n}O \cdot Al_2O_3 \cdot xSiO_2 \cdot yH_2O$$

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

MTBE can also be manufactured by the reaction of isobutylene with methanol. For example, the reaction of isobutylene with methanol to form MTBE is disclosed in Kruse U.S. Pat. No. 5,243,091, Cassata et al. U.S. Pat. No. 5,395,982, Hwan et al. U.S. Pat. No. 5,395,982, etc.

Two of the principal by-products formed during the reaction of the methanol with the tertiary butyl alcohol are water and isobutylene. The separation of MTBE from methanol during the recovery of purified MTBE presents a serious problem.

In U.S. Pat. No. 4,820,877, separation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of crosslinked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to form an azeotrope with methanol. This azeotrope is recovered overhead giving a methanol-free MTBE bottoms product.

As recognized by Rao et al. in U.S. Pat. No. 4,144,138, isobutylene is formed as a by-product when methanol is reacted with tertiary butyl alcohol. In accordance with the Rao process, the isobutylene is separated from the reaction product in an initial azeotropic distillation step as a noncondensable gas. Rao teach that part of the isobutylene may be flashed from the reaction product for recycle, depending upon purity.

SUMMARY OF THE INVENTION

The present invention is directed to a method for preparing methyl tertiary butyl ether and diisobutylene from methanol and tertiary butyl alcohol by a process wherein methanol is reacted with tertiary butyl alcohol to provide an etherification reaction product containing methyl tertiary butyl ether, tertiary butyl alcohol, methanol, isobutylene, and water including the steps of (a) recovering a methyl tertiary butyl ether product fraction and an isobutylene fraction from the etherification reaction product, b) charging the isobutylene fraction to an isobutylene conversion reaction zone and contacting it therein with a solid resin etherification catalyst to form a diisobutylene conversion product, and (c) charging the diisobutylene conversion product to a diisobutylene distillation zone and separating it therein into a lower boiling (lighter) distillation fraction comprising isobutylene, methyl tertiary butyl ether and diisobutylene and a higher boiling (heavier) distillation fraction consisting essentially of diisobutylene.

I

In accordance with a preferred embodiment of the present invention, the etherification reaction product (which contains methyl tertiary butyl ether, tertiary butyl alcohol, methanol, isobutylene, oxygenated by-products and water) is fractionated in a primary methyl tertiary butyl ether distillation zone to obtain a first lower boiling (lighter) fraction comprising methyl tertiary butyl ether, methanol and isobutylene and a first higher boiling (heavier) fraction comprising tertiary butyl alcohol, methanol, oxygenated by-products and water;

the first lower boiling (lighter) fraction is countercurrently contacted with water in a methanol extraction tower to provide an overhead extract comprising isobutylene, methyl tertiary butyl ether and water, and a bottoms raffinate comprising methanol and water;

the extract is charged to a methyl tertiary butyl ether distillation zone and separated therein into a second lower boiling (lighter) distillation fraction comprising isobutylene a water distillation fraction and a second higher boiling (heavier) distillation fraction consisting essentially of methyl tertiary butyl ether;

the isobutylene fraction is continuously charged to an isobutylene conversion reaction zone and contacted therein with a solid resin etherification catalyst to convert isobutylene to diisobutylene and to form a diisobutylene conversion product; and the diisobutylene conversion product is continuously charged to a diisobutylene distillation zone and separated therein into a third lower boiling (lighter) distillation fraction comprising isobutylene, and diisobutylene and a third higher boiling (heavier) distillation fraction consisting essentially of diisobutylene.

II

In accordance with another preferred embodiment of the present invention, the primary etherification reaction product prepared by reacting methanol with tertiary butyl alcohol is fractionated in a primary methyl tertiary butyl ether distillation zone to obtain a first lower boiling (lighter) fraction comprising methyl tertiary butyl ether, methanol and isobutylene and a first higher boiling (heavier) fraction comprising tertiary butyl alcohol, methanol, oxygenated by-products and water;

the first lower boiling (lighter) fraction is countercurrently contacted with water in a methanol extraction tower to provide an overhead extract comprising isobutylene, methyl tertiary butyl ether and water, and a bottoms raffinate comprising methanol and water;

the extract is charged to a methyl tertiary butyl ether purification distillation zone and separated therein into a second lower boiling (lighter) distillation fraction comprising isobutylene and water and a second higher boiling (heavier) distillation fraction consisting essentially of methyl tertiary butyl ether;

the second lower boiling (lighter) distillation fraction is charged to a decantation separation zone and separated therein into an isobutylene fraction and a water fraction;

the isobutylene fraction is charged to an isobutylene conversion reaction zone and contacted therein with a solid resin etherification catalyst to convert isobutylene to diisobutylene and to form a diisobutylene conversion product;

the diisobutylene conversion product is charged to a diisobutylene distillation zone and separating it therein into a third lower boiling (lighter) distillation fraction comprising isobutylene, and diisobutylene and a third higher boiling (heavier) distillation fraction consisting essentially of diisobutylene.

III

In accordance with a more preferred embodiment of the present invention, methanol is reacted with tertiary butyl alcohol in an etherification reaction zone to provide an etherification reaction product containing methyl tertiary butyl ether, tertiary butyl alcohol, methanol, isobutylene, oxygenated by-products, including dimethyl ether and water;

the etherification reaction product is fractionated in a primary methyl tertiary butyl ether distillation zone under distillation conditions including a reflux temperature of about 30° to about 60° C., a reboiler temperature of about 80° to about 115°C. and a pressure of about 15 to about 60 psia to obtain a first lower boiling (lighter) fraction comprising methyl tertiary butyl ether, methanol dimethyl ether and isobutylene and a first higher boiling (heavier) fraction comprising tertiary butyl alcohol, methanol, oxygenated by-products and water;

the lower boiling (lighter) fraction is counter-currently contacted with water in a methanol extraction tower to provide an overhead extract comprising isobutylene, dimethyl ether, methyl tertiary butyl ether and water, and a bottoms raffinate comprising methanol and water under extraction conditions including a ratio of about 0.8 to about 1.8 volumes of said first lower boiling (lighter) fraction per volume of water, a temperature of about 20° to about 60°C. and a pressure of about 50 to 500 psia.;

the extract is continuously charged to a methyl tertiary butyl ether purification distillation column and separated therein under distillation conditions including a reflux temperature of about 30° to about 60° C., a reboiler temperature of about 100° to about 140° C. and a pressure of about 70 to about 110 psia into an overhead distillation fraction comprising isobutylene and water, a second lower boiling (lighter) recycle fraction comprising isobutylene, dimethyl ether and water and a second higher boiling (heavier) distillation fraction consisting essentially of methyl tertiary butyl ether;

the overhead distillation fraction is continuously charged to a decantation separation zone and separated therein into an isobutylene fraction and a water fraction;

the isobutylene fraction is continuously charged to an isobutylene conversion reaction zone and contacted therein with a solid resin etherification catalyst to convert isobutylene to diisobutylene and to form a diisobutylene conversion product;

the diisobutylene conversion product is continuously charged to a diisobutylene distillation column and separated therein under distillation conditions including a reflux temperature of about 30° to about 60° C., a reboiler temperature of about 100° to about 140° C. and a pressure of about 70 to about 110 psia into a third lower boiling (lighter) distillation fraction comprising isobutylene and diisobutylene and a third higher boiling (heavier) distillation fraction consisting essentially of diisobutylene;

the second lower boiling (lighter) fraction is recycled to the methanol extraction tower; and the third lower boiling (lighter) distillation fraction is recycled to the primary methyl tertiary butyl ether distillation column.

DETAILED DESCRIPTION OF THE PRESENT INVENTION

The Etherification Reaction Catalyst

In accordance with the MTBE manufacture and purification method of the present invention, an etherification reaction zone containing a bed of etherification catalyst is utilized. A wide variety of etherification catalysts can be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138. A solid acidic catalyst may be used, such as Kieselguhr impregnated with a phosphoric acid as disclosed in Frolich U.S. Pat. No. 2,282,469, zeolites as disclosed in Japanese Patent 0007432, aluminosilicate zeolites as disclosed in Chang et al. U.S. Pat. No. 4,058,576, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc.

The reaction conditions to be utilized when reacting methanol with tertiary butyl alcohol in the presence of an etherification catalyst of the type disclosed include a reaction temperature of about 90° to about 140° C., a pressure of about 30 to about 500 psia and a flow rate of about 0.5 to about 20 volumes of feed per volume of etherification catalyst per hour.

The Solid Resin Etherification Catalyst

In accordance with the present invention, methyl tertiary butyl ether and isobutylene are separately recovered from the primary reaction product and the recovered isobutylene and methanol are brought into contact with a solid resin etherification catalyst in order to convert a significant portion of the isobutylene and methanol to methyl tertiary butyl ether.

Any suitable solid resin etherification catalyst may be used for this purpose, such as a strongly acidic ion exchange resin consisting essentially of sulfonated polystyrene, such a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

The isobutylene and methanol are brought into contact with a solid resin etherification catalyst in an isobutylene conversion reaction zone under conversion conditions including, for example, a temperature of about 20° to about 130° C., a pressure of about 50 to about 500 psia and a flow rate of about 1 to about 10 volumes of isobutylene/methanol feed per volume of etherification catalyst per hour.

BRIEF DESCRIPTION OF THE DRAWING

The drawing is a schematic flow sheet with conventional parts omitted showing the general reaction and recovery sequence of the present invention for the manufacture and purification of methyl tertiary butyl ether and diisobutylene.

DESCRIPTION OF THE PREFERRED EMBODIMENT

Turning now to the drawing, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary etherification reaction zone 10 containing a bed of a solid etherification catalyst, such as a catalyst, a solid resin etherification catalyst (e.g., a strongly acidic ion exchange resin consisting essentially of sulfonated polystyrene, such a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15".

Substantially peroxide-free tertiary butyl alcohol is continuously charged to the etherification reaction zone 10 by a line 12. Methanol is charged to the reactor 10 by a line 16. The flow of methanol and tertiary butyl alcohol to the etherification reaction zone 10 is regulated so that a molar excess of methanol is present such as, for example, a molar ratio of about 1.1 to about 3 moles of methanol per mol of tertiary butyl alcohol.

Within the etherification reaction zone 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., a still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will exothermically react with the tertiary butyl alcohol to form methyl tertiary butyl ether which will be contained in a reaction product discharged from the etherification reaction zone 10 by way of a line 20 leading to a primary methyl tertiary butyl ether (MTBE) distillation zone 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 contains about 2.0 moles of methanol per mole of tertiary butyl alcohol, and the reaction is conducted at a temperature of about 100° C. at a feed rate of about 2.0 volumes of feed mixture per volume of catalyst per hour, a representative etherification reaction product will have the composition shown by the following table:

| ETHERIFICATION REACTION PRODUCT | |
| --- | --- |
| Component | wt. % |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, ditertiary butyl peroxide, tertiary butyl formate, etc., initially present in the tertiary butyl alcohol feedstock.

The etherification reaction product charged to the first MTBE distillation zone 30 by way of the charge line 20 is fractionated therein under distillation conditions including a liquid reflux temperature of about 25° to about 100° C., and more preferably about 30° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reactor 10 is taken overhead from the first distillation zone 30 by a line 32 and such that substantially all of the tertiary butyl alcohol exits the column 30 through the line 34. As a consequence, the first lower boiling (lighter) distillation fraction 32 taken overhead from the distillation zone 30 will comprise substantially all of the isobutylene, methyl tertiary butyl ether and DME and some of the methanol and water charged to the first distillation zone 30. The first higher boiling (heavier) distillation fraction 34 discharged from the first distillation zone 30 will comprise methanol, tertiary butyl alcohol and water.

In accordance with the present invention, the first lower boiling (lighter) distillation fraction 32 together with recycle water, isobutylene and dimethyl ether in recycle line 65 is charged to a methanol solvent extraction zone 50 where it is countercurrently contacted with water introduced into the solvent extraction zone 50 by a charge line 52 controlled by a valve 54.

Within the methanol solvent extraction zone 50, solvent extraction conditions are established for countercurrent solvent extraction including a ratio of hydrocarbon feed to water within the range of about 0.8 to 1.8 volumes of hydrocarbon per volume of water per hour, and more preferably, a ratio of about 1.0 to about 1.5 volumes of hydrocarbon per volume of water per hour. Extraction conditions to be established may suitably include a temperature of about 20° to about 60° C., and more preferably, from about 30° to about 40° C., and a pressure of about 50 to 500 psia, and more preferably from about 50 to 150 psia.

As a consequence, a supernatant extract will be formed which is withdrawn from the methanol solvent extraction zone 50 by line 60 leading to a methyl tertiary butyl ether purification distillation column 62. The raffinate is discharged from the solvent extraction zone 50 by way of a bottoms discharge line 68.

Within the methyl tertiary butyl ether purification distillation column 62, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form an overhead distillation fraction 64, a second lower boiling (lighter) distillation fraction 65 and a second higher boiling (heavier) distillation fraction 68 consisting essentially of product, namely, methyl tertiary butyl ether substantially free from tertiary butyl alcohol and isobutylene.

The second lower boiling (lighter) distillation fraction 65 will comprise a mixture of water, isobutylene and dimethyl ether and is suitably recycled to the methanol extraction column 50.

The overhead distillation fraction 64 will comprise a mixture of water and isobutylene and suitably may be cooled in heat exchanger 67 and then charged to a decantation zone 80 where it can settle to form a supernatant isobutylene phase withdrawn by way of a line 82 and a water phase withdrawn by way of a water discharge line 84 and suitably purged from the system.

A portion of the isobutylene in the line 82 is recycled to the MTBE purification distillation column 62 as reflux by the line 83. The major portion of the isobutylene in the line 82 is charged by lines 85 and 87 to an isobutylene conversion zone 100 for conversion to diisobutylene. The dimerization of diisobutylene is a known reaction and can be conducted thermally in the optional presence of a catalyst. A diisobutylene reaction product is formed, which is discharged from the reactor 100 by a line 102.

A minor portion of the diisobutylene reaction product 102 is recycled by a line 104 to a heat-exchanger 106 where the recycle fraction 104 is cooled. The cooled recycle stream is charged by line 107 to the feed line 87 for the isobutylene conversion reactor 100.

The major portion of the diisobutylene reaction product 102 is charged by a line 110 to a diisobutylene distillation column 120 where it is separated into a third lower boiling (lighter) distillation fraction 122 comprising a mixture of isobutylene and diisobutylene that is recycled to the methyl tertiary butyl ether purification column 62 and a third higher boiling (heavier) distillation fraction 124 consisting essentially of diisobutylene that is recovered as product.

Having thus described our invention, what is claimed is:

1. A method for preparing methyl tertiary butyl ether and diisobutylene from methanol and tertiary butyl alcohol by a process wherein methanol is reacted with tertiary butyl alcohol to provide an etherification reaction product containing methyl tertiary butyl ether, tertiary butyl alcohol, methanol, isobutylene, oxygenated by-products and water which comprises the steps of:
   a) recovering a methyl tertiary butyl ether product fraction and an isobutylene fraction from said etherification reaction product,
   b) charging said isobutylene fraction to an isobutylene conversion reaction zone and contacting it therein with a solid resin etherification catalyst to convert isobutylene to diisobutylene and to form a diisobutylene conversion product containing isobutylene, methyl tertiary butyl ether and diisobutylene, and
   c) charging said diisobutylene conversion product to a diisobutylene distillation zone and separating it therein into a lower boiling distillation fraction comprising isobutylene, and diisobutylene and a higher boiling distillation fraction consisting essentially of diisobutylene.

2. A method as in claim 1 wherein the solid resin etherification catalyst is a strongly acidic ion exchange resin consisting essentially of a divinyl benzene crosslinked polystyrene matrix copolymerized with divinyl benzene.

3. A method for preparing methyl tertiary butyl ether and diisobutylene from methanol and tertiary butyl alcohol by a process wherein methanol is reacted with tertiary butyl alcohol to provide an etherification reaction product containing methyl tertiary butyl ether, tertiary butyl alcohol, methanol, isobutylene, oxygenated by-products including dimethyl ether and water which comprises the steps of:
   a) fractionating the etherification reaction product in a primary methyl tertiary butyl ether distillation zone to obtain a first lower boiling fraction comprising methyl tertiary butyl ether, methanol, dimethyl ether and isobutylene and a first higher boiling fraction comprising tertiary butyl alcohol, methanol, oxygenated by-products and water,
   b) countercurrently washing said first lower boiling fraction with water in a methanol extraction tower to provide an overhead extract comprising isobutylene, methyl tertiary butyl ether, dimethyl ether and water, and a bottoms raffinate comprising methanol and water,
   c) charging said extract to a methyl tertiary butyl ether distillation zone and separating it therein into a second lower boiling distillation fraction comprising isobutylene and water and a second higher boiling distillation fraction consisting essentially of methyl tertiary butyl ether,
   d) charging said second lower boiling distillation fraction to a decantation separation zone and separating it therein into an isobutylene fraction and a water fraction,
   e) charging said isobutylene fraction to an isobutylene conversion reaction zone and contacting it therein with a solid resin etherification catalyst to convert isobutylene to diisobutylene and to form a conversion product containing diisobutylene,
   f) charging said conversion product to a diisobutylene distillation zone and separating it therein into a third lower boiling distillation fraction comprising isobutylene, methyl tertiary butyl ether and diisobutylene and a third higher boiling distillation fraction consisting essentially of diisobutylene.

4. A method as in claim 3 wherein the solid resin etherification catalyst is a strongly acidic ion exchange resin consisting essentially of a divinyl benzene crosslinked polystyrene matrix copolymerized with divinyl benzene.

5. A method as in claim 3 wherein the third lower boiling distillation fraction is recycled to the methyl tertiary butyl ether distillation column.

6. A method for preparing methyl tertiary butyl ether and diisobutylene from methanol and tertiary butyl alcohol by a process wherein methanol is reacted with tertiary butyl alcohol to provide an etherification reaction product containing methyl tertiary butyl ether, tertiary butyl alcohol, methanol, isobutylene, oxygenated by-products and water which comprises the steps of:
   a) fractionating the etherification reaction product to obtain a first lower boiling fraction comprising methyl tertiary butyl ether, methanol, dimethyl ether and isobutylene and a first higher boiling fraction comprising tertiary butyl alcohol, methanol, oxygenated by-products and water,
   b) countercurrently washing said first lower boiling fraction with water in a methanol extraction tower to provide an overhead extract comprising isobutylene, dimethyl ether, methyl tertiary butyl ether and water, and a bottoms raffinate comprising methanol and water,
   c) continuously charging said extract to a methyl tertiary butyl ether distillation column and separating it therein into an overhead distillation fraction comprising isobutylene and water, a second lower boiling recycle fraction comprising isobutylene, dimethyl ether and water and a second higher boiling distillation fraction consisting essentially of methyl tertiary butyl ether,
   d) charging said overhead distillation fraction to a decantation separation zone and separating it therein into an isobutylene fraction and a water fraction,
   e) charging said isobutylene fraction to an isobutylene conversion reaction zone and contacting it therein with a solid resin etherification catalyst to convert isobutylene to diisobutylene and to form a diisobutylene conversion product containing isobutylene, methyl tertiary butyl ether and diisobutylene,
   f) charging said diisobutylene conversion product to a diisobutylene distillation column and separating it therein into a third lower boiling distillation fraction comprising isobutylene, methyl tertiary butyl ether and diisobutylene and a third higher boiling distillation fraction consisting essentially of diisobutylene,
   g) recycling said second lower boiling recycle fraction to said methanol extraction tower, and
   h) recycling said third lower boiling distillation fraction to said methyl tertiary butyl ether distillation column.

7. A method for preparing methyl tertiary butyl ether and diisobutylene from methanol and tertiary butyl alcohol by a process wherein methanol is reacted with tertiary butyl alcohol to provide an etherification reaction product containing methyl tertiary butyl ether, tertiary butyl alcohol, methanol, isobutylene, oxygenated by-products and water which comprises the steps of:
   a) fractionating the etherification reaction product under distillation conditions including a reflux temperature of about 30° to about 60° C., a reboiler temperature of about 80° to about 115° C. and a pressure of about 15 to about 60 psia to obtain a first lower boiling fraction comprising methyl tertiary butyl ether, methanol, dimethyl ether and isobutylene and a first higher boiling fraction comprising tertiary butyl alcohol, methanol, oxygenated by-products and water,
   b) countercurrently washing said first lower boiling fraction with water in a methanol extraction tower under extraction condition including a ratio of about 0.8 to about 1.8 volumes of said first lower boiling fraction per volume of water, a temperature of about 20° to about 60° C. And a pressure of about 50 to about 500 psia to provide an overhead extract comprising isobutylene, dimethyl ether, methyl tertiary butyl ether and water, and a bottoms raffinate comprising methanol and water, c) charging said extract to a methyl tertiary butyl ether distillation column and separating it therein under distillation conditions including a reflux temperature of about 30° to about 60° C., a reboiler temperature of about 100° to about 140° C. and a pressure of about 70 to about 110 psia into an overhead distillation fraction comprising isobutylene and water, a second lower boiling recycle fraction comprising isobutylene, dimethyl ether and water and a second higher boiling distillation fraction consisting essentially of methyl tertiary butyl ether, d) charging said overhead distillation fraction to a decantation separation zone and separating it therein into an isobutylene fraction and a water fraction, e) charging said isobutylene fraction to an isobutylene conversion reaction zone and contacting it therein with a solid resin etherification catalyst to convert isobutylene to diisobutylene and to form a conversion product containing isobutylene, methyl tertiary butyl ether and diisobutylene, f) charging said conversion product to a diisobutylene distillation column and separating it therein under distillation conditions including a reflux temperature of about 30° to about 60 C., a reboiler temperature of about 100° to about 140° C. and a pressure of about 70 to about 110 psia into a third lower boiling distillation fraction comprising isobutylene, methyl tertiary butyl ether and diisobutylene and a third higher boiling distillation fraction consisting essentially of diisobutylene, g) recycling said second lower boiling recycle fraction to said methanol extraction tower, and h) recycling said third lower boiling distillation fraction to said methyl tertiary butyl ether distillation column.

\* \* \* \* \*